(12) United States Patent
Tani

(10) Patent No.: US 11,336,825 B2
(45) Date of Patent: May 17, 2022

(54) ENDOSCOPE APPARATUS, ENDOSCOPE AND VIDEO PROCESSOR, AND RESTORATION METHOD

(71) Applicant: OLYMPUS CORPORATION, Tokyo (JP)

(72) Inventor: Shinsuke Tani, Tachikawa (JP)

(73) Assignee: OLYMPUS CORPORATION, Tokyo (JP)

(*) Notice: Subject to any disclaimer, the term of this patent is extended or adjusted under 35 U.S.C. 154(b) by 82 days.

(21) Appl. No.: 17/083,632

(22) Filed: Oct. 29, 2020

(65) Prior Publication Data

US 2021/0195115 A1  Jun. 24, 2021

Related U.S. Application Data

(63) Continuation of application No. PCT/JP2019/007108, filed on Feb. 25, 2019.

(30) Foreign Application Priority Data

May 1, 2018 (JP) .............................. JP2018-088335

(51) Int. Cl.
  *H04N 5/225* (2006.01)
  *H04N 1/04* (2006.01)
  (Continued)

(52) U.S. Cl.
  CPC ... *H04N 5/232411* (2018.08); *A61B 1/00006* (2013.01); *A61B 1/00009* (2013.01);
  (Continued)

(58) Field of Classification Search
  CPC ........... H04N 5/232411; H04N 5/2256; H04N 2005/2255; H04N 5/23203;
  (Continued)

(56) References Cited

U.S. PATENT DOCUMENTS

| 2010/0179834 A1 | 7/2010 | Wager |
| 2010/0179835 A1 | 7/2010 | Wager |

(Continued)

FOREIGN PATENT DOCUMENTS

| EP | 3047789 A1 | 7/2016 |
| EP | 3222199 A1 | 9/2017 |

(Continued)

OTHER PUBLICATIONS

International Search Report dated May 7, 2019 issued in PCT/JP2019/007108.

*Primary Examiner* — Alazar Tilahun

(74) *Attorney, Agent, or Firm* — Scully, Scott, Murphy & Presser, P.C.

(57) ABSTRACT

An endoscope apparatus includes an image pickup device, an illumination element, a power source unit, a processor, an image processing unit, and a monitor as a display unit. The illumination element is capable of executing illumination light reduction processing. The image pickup device is capable of executing frame rate reduction processing and pixel count reduction processing. When the processor selects a low power consumption operation mode, at least one of the illumination light reduction processing, the frame rate reduction processing and the pixel count reduction processing is executed, and the image processing unit performs image restoration processing relevant to the illumination light reduction processing, the frame rate reduction processing and the pixel count reduction processing.

12 Claims, 11 Drawing Sheets

(51) Int. Cl.
*A61B 1/06* (2006.01)
*A61B 1/00* (2006.01)
*A61B 1/04* (2006.01)
*H04N 5/232* (2006.01)

(52) U.S. Cl.
CPC ...... *A61B 1/00032* (2013.01); *A61B 1/00036* (2013.01); *A61B 1/00045* (2013.01); *A61B 1/00114* (2013.01); *A61B 1/04* (2013.01); *A61B 1/06* (2013.01); *H04N 5/2256* (2013.01); *H04N 2005/2255* (2013.01)

(58) Field of Classification Search
CPC ............ H04N 5/23241; A61B 1/00006; A61B 1/00009; A61B 1/00032; A61B 1/00036; A61B 1/00045; A61B 1/00114; A61B 1/04; A61B 1/06; A61B 1/045
See application file for complete search history.

(56) References Cited

U.S. PATENT DOCUMENTS

2016/0248974 A1* 8/2016 Tabuchi .............. A61B 1/00006
2017/0231472 A1* 8/2017 Nishio ................. A61B 1/0676
                                                              348/68
2017/0251904 A1* 9/2017 Kasumi ............ H04N 5/232411

FOREIGN PATENT DOCUMENTS

| JP | 2016-101377 A | 6/2016 |
|----|---------------|--------|
| WO | 2015/119070 A1 | 8/2015 |
| WO | 2016/071991 A1 | 5/2016 |
| WO | 2017/029839 A1 | 2/2017 |
| WO | 2018/021034 A1 | 2/2018 |

* cited by examiner

ENDOSCOPE APPARATUS, ENDOSCOPE AND VIDEO PROCESSOR, AND RESTORATION METHOD

CROSS REFERENCE TO RELATED APPLICATION

This application is a continuation application of PCT/JP2019/007108 filed on Feb. 25, 2019 and claims benefit of Japanese Application No. 2018-088335 filed in Japan on May 1, 2018, the entire contents of which are incorporated herein by this reference.

BACKGROUND OF THE INVENTION

1. Field of the Invention

The present invention relates to an endoscope apparatus capable of executing low power consumption processing, an endoscope and a video processor, and a restoration method.

2. Description of the Related Art

In recent years, endoscope apparatuses have been widely employed in medical and industrial fields. In particular, endoscopes used in the medical field are widely used for observation of organs in body cavities, treatment procedures using treatment instruments, surgeries under observation with endoscopes and the like.

Along with advancement in semiconductor technology and power saving achieved by use of LEDs as illumination light sources, battery-driven endoscopes that incorporate rechargeable batteries are also finding their ways into practical use today. A battery-driven endoscope contains a wireless communication unit for performing wireless communication with a processor, and is configured to wirelessly transmit image data obtained by performing image pickup with an image pickup device.

For a battery-driven endoscope, it is desirable that the endoscope is capable of executing low power consumption processing which reduces power consumption of the endoscope in order to reduce an amount of consumption of the battery or to extract the endoscope safely from a body when a level of the battery is running low. The capability to execute low power consumption processing is also desirable for an endoscope apparatus configured with an endoscope and a processor connected by a universal cable, from the perspective of longer service lives of components and the like.

International Publication No. WO2017/029839 discloses a wireless endoscope that effects power saving operations, such as decreasing a shooting frame rate, increasing an image compression rate and reducing illumination light quantity, during change of a battery.

SUMMARY OF THE INVENTION

An endoscope apparatus according to an aspect of the present invention includes: an image pickup device configured to perform image pickup of an object and generate image data; an illumination element configured to illuminate the object; a power source configured to supply electric power to the image pickup device and the illumination element; a monitor configured to display a display image corresponding to the image data; and a processor, where the processor is configured to perform selection processing for selecting between a normal operation mode and a low power consumption operation mode in which low power consumption processing is executed, and perform image processing on the image data; the illumination element is capable of executing, as the low power consumption processing, illumination light reduction processing which reduces illumination light compared to when the processor selects the normal operation mode; the image pickup device is capable of executing, as the low power consumption processing, frame rate reduction processing which reduces a frame rate of the image data compared to when the processor selects the normal operation mode, and pixel count reduction processing which reduces a pixel count of the image data compared to when the processor selects the normal operation mode; and when the processor selects the low power consumption operation mode, at least one of the illumination light reduction processing, the frame rate reduction processing and the pixel count reduction processing is executed, and the processor detects which one or ones of the illumination light reduction processing, the frame rate reduction processing and the pixel count reduction processing is or are executed as the low power consumption processing and performs image restoration processing for improving an image quality of the display image in accordance with an obtained detection result.

An endoscope apparatus according to another aspect of the present invention includes: an endoscope; a video processor physically separated from the endoscope; and a monitor configured to display a display image corresponding to image data obtained by performing image pickup with the endoscope, where the endoscope includes: an image pickup device configured to perform image pickup of an object and generate the image data; an illumination element configured to illuminate the object; a power source configured to supply electric power to the image pickup device and the illumination element; a first processor; and a first wireless communication circuit, where the first processor is configured to perform selection processing for selecting between a normal operation mode and a low power consumption operation mode in which low power consumption processing is executed, compress the image data to generate compressed data, and judge whether an execution condition of the low power consumption operation mode is met or not; the first wireless communication circuit transmits the compressed data and information on specifics of the low power consumption processing; the video processor includes: a second wireless communication circuit configured to receive the transmitted compressed data and information on specifics of the low power consumption processing; and a second processor; the second processor is configured to perform image processing on the image data generated by decompressing the compressed data, and judge whether the execution condition of the low power consumption operation mode is met or not; the first processor detects a quantity of state associated with the execution condition of the low power consumption operation mode, and judges whether the execution condition of the low power consumption operation mode is met or not based on an obtained detection result; the second processor detects a quantity of state associated with the execution condition of the low power consumption operation mode, judges whether the execution condition of the low power consumption operation mode is met or not based on an obtained detection result, and outputs an obtained judgement result to the first processor via wireless communication between the first wireless communication circuit and the second wireless communication circuit; and the first processor performs the selection processing based on at least one of the judgement result from the first processor and the judgement result from the second processor.

An endoscope according to an aspect of the present invention includes: an image pickup device configured to perform image pickup of an object and generate image data; an illumination element configured to illuminate the object; a power source configured to supply electric power to the image pickup device and the illumination element; and a processor configured to perform selection processing for selecting between a normal operation mode and a low power consumption operation mode in which low power consumption processing is executed, where the illumination element is capable of executing, as the low power consumption processing, illumination light reduction processing which reduces illumination light compared to when the processor selects the normal operation mode; the image pickup device is capable of executing, as the low power consumption processing, frame rate reduction processing which reduces a frame rate of the image data compared to when the processor selects the normal operation mode, and pixel count reduction processing which reduces a pixel count of the image data compared to when the selection unit selects the normal operation mode; and when the processor selects the low power consumption operation mode, at least one of the illumination light reduction processing, the frame rate reduction processing and the pixel count reduction processing is executed; and the processor outputs information on specifics of the low power consumption processing to a video processor connected with a display unit configured to display a display image corresponding to the image data so that the video processor can detect which one or ones of the illumination light reduction processing, the frame rate reduction processing and the pixel count reduction processing is or are executed as the low power consumption processing and perform image restoration processing for improving an image quality of the display image in accordance with an obtained detection result.

A video processor according to an aspect of the present invention is a video processor connected with a monitor configured to display a display image corresponding to image data generated by an endoscope, the video processor including: a processor configured to receive the image data transmitted by the endoscope and to perform image processing on the image data; where the endoscope is capable of executing, as low power consumption processing, illumination light reduction processing which reduces illumination light of an illumination element of the endoscope, frame rate reduction processing which reduces a frame rate of the image data, and pixel count reduction processing which reduces a pixel count of the image data, and outputs information on specifics of the low power consumption processing to the processor; and the processor detects which one or ones of the illumination light reduction processing, the frame rate reduction processing and the pixel count reduction processing is or are executed as the low power consumption processing, and performs image restoration processing for improving an image quality of the display image in accordance with an obtained detection result.

A restoration method according to an aspect of the present invention is a restoration method for restoring image data acquired with an image pickup device of an endoscope, the restoration method including: performing selection processing for selecting between a normal operation mode and a low power consumption operation mode in which low power consumption processing is executed, as an operation mode in which electric power is supplied to the image pickup device and an illumination element of the endoscope; performing image processing on the image data; and displaying a display image corresponding to the image data, where the illumination element is capable of executing, as the low power consumption processing, illumination light reduction processing which reduces illumination light compared to when the normal operation mode is selected; and the image pickup device is capable of executing, as the low power consumption processing, frame rate reduction processing which reduces a frame rate of the image data compared to when the normal operation mode is selected, and pixel count reduction processing which reduces a pixel count of the image data compared to when the normal operation mode is selected, and the restoration method further includes: when the low power consumption operation mode is selected, executing at least one of the illumination light reduction processing, the frame rate reduction processing and the pixel count reduction processing, detecting which one or ones of the illumination light reduction processing, the frame rate reduction processing and the pixel count reduction processing is or are executed as the low power consumption processing, and performing image restoration processing for improving an image quality of the display image in accordance with an obtained detection result.

DETAILED DESCRIPTION OF THE PREFERRED EMBODIMENTS

Embodiments of the present invention are now described with reference to the drawings.

First Embodiment

Configuration of an Endoscope Apparatus

Figure 1:
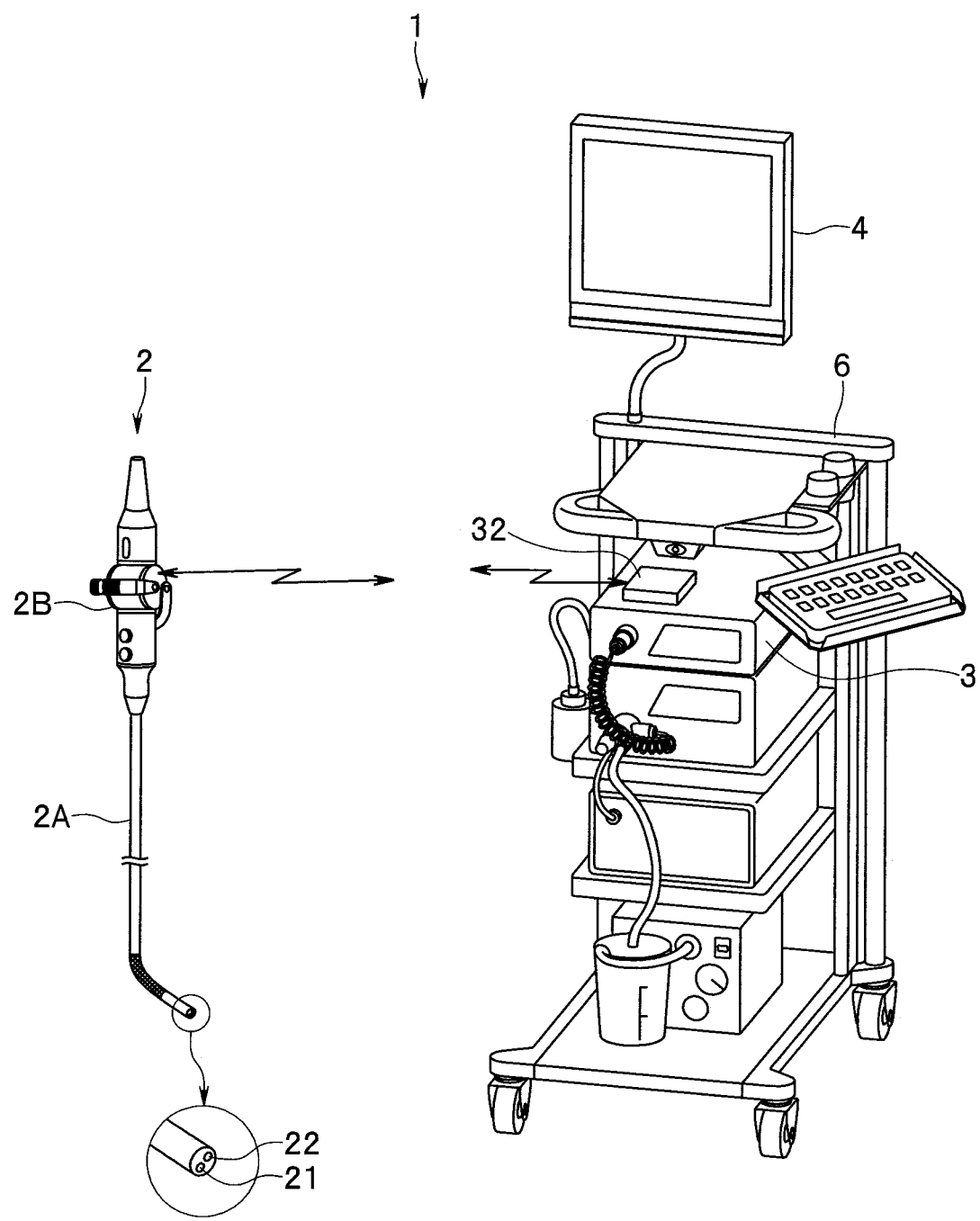
FIG. 1 is an illustrative diagram showing an overall configuration of an endoscope apparatus according to a first embodiment of the present invention.

First, a general configuration of an endoscope apparatus according to a first embodiment of the present invention is described. FIG. 1 is an illustrative diagram showing an overall configuration of an endoscope apparatus 1 according to the present embodiment. The endoscope apparatus 1 according to the present embodiment is a wireless endoscope apparatus including a wireless endoscope 2, which is a battery-driven, portable endoscope. Hereinafter, the wireless endoscope 2 will be denoted just as an endoscope 2.

The endoscope apparatus 1 further includes a processor 3 as a video processor physically separated from the endoscope 2, and a monitor 4 as a display unit connected with the processor 3. The processor 3 is connected with the endoscope 2 by radio and performs predetermined image processing as discussed later. The monitor 4 displays results of image processing, more specifically, images obtained by performing image pickup with the endoscope 2 and the like.

Note that in an operation room, the processor 3, the monitor 4 and various medical devices are placed on a cart 6 as shown in FIG. 1. The medical devices which can be placed on the cart 6 include devices such as an electrocautery device, a pneumoperitoneum device and a video recorder, a gas cylinder filled with carbon dioxide, for example.

The endoscope 2 includes an elongated insertion portion 2A for insertion into a body cavity, an operation portion 2B provided at a proximal end portion of the insertion portion 2A, an image pickup unit 21 configured to perform image pickup of an object and generate image data, and an illumination unit 22 configured to illuminate the object. The object can be an area such as an affected area within a subject, for example. The image pickup unit 21 includes an image pickup device, not shown, such as a CCD or CMOS provided at a distal end portion of the insertion portion 2A.

The illumination unit 22 is formed from a light emitting element, not shown, such as a light emitting diode, and a lens, not shown, provided at the distal end of the insertion portion 2A. Illumination light emitted by the light emitting element is applied to the object via the lens. On an image pickup surface of the image pickup device of the image pickup unit 21, return light from the object produced by the illumination light forms an image. Note that the light emitting element may be provided in the operation portion 2B. In that case, the illumination light emitted by the light emitting element is guided to the distal end of the insertion portion 2A by a light guide not shown.

Figure 2:
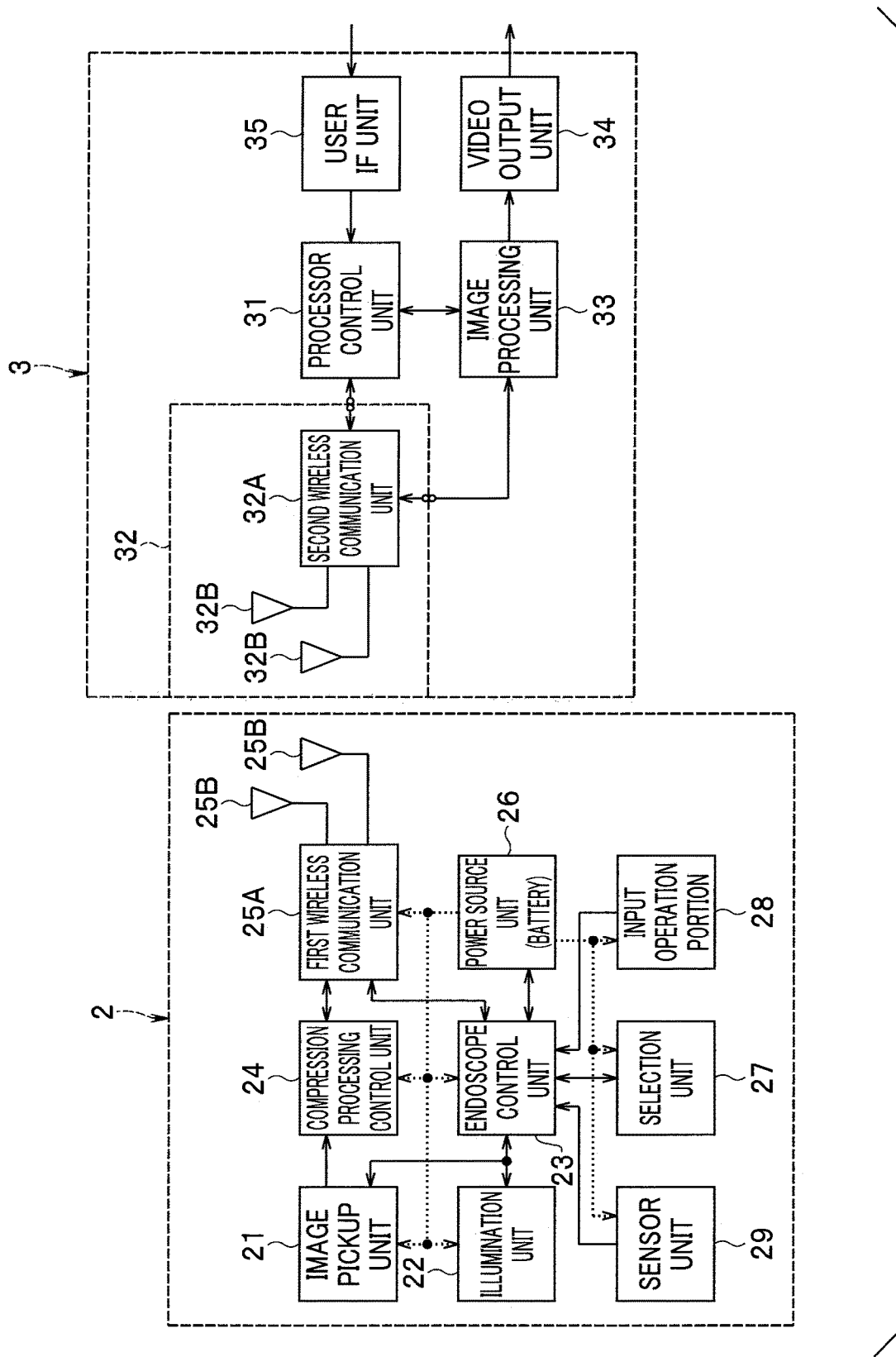
FIG. 2 is a functional block diagram showing configurations of an endoscope of and a processor of the endoscope apparatus in the first embodiment of the present invention.

Now referring to FIG. 2, configurations of the endoscope 2 and the processor 3 are described in detail. FIG. 2 is a functional block diagram showing configurations of the endoscope 2 and the processor 3.

Configuration of the Endoscope

First, the configuration of the endoscope 2 is described. As shown in FIG. 2, the endoscope 2 includes the image pickup unit 21 and the illumination unit 22 described above, an endoscope control unit 23, a compression processing control unit 24, a first wireless communication unit 25A, an antenna 25B, a power source unit 26, a selection unit 27, an input operation portion 28, and a sensor unit 29.

In the present embodiment, the power source unit 26 is composed of a battery mountable to the operation portion 2B (see FIG. 1). The battery as mounted in the operation portion 2B is configured to be able to supply, as the power source unit 26, electric power to the image pickup unit 21, the illumination unit 22, the endoscope control unit 23, the compression processing control unit 24, the first wireless communication unit 25A, the selection unit 27, the input operation portion 28 and the sensor unit 29. The power source unit 26 also outputs a battery level signal indicating the level of the battery to the endoscope control unit 23.

The endoscope control unit 23 controls each circuit unit in the endoscope 2 and controls the power source unit 26 to make the power source unit 26 supply electric power to different parts in the endoscope 2. The endoscope control unit 23 is composed of a processor including hardware, such as a central processing unit (hereinafter denoted as CPU) or a digital signal processor (hereinafter denoted as DSP).

The image pickup unit 21 generates image data based on an optical image of the object via photoelectric conversion and outputs the image data to the endoscope control unit 23 and the compression processing control unit 24. The compression processing control unit 24 performs compression processing, which applies predetermined compression processing to the image data generated by the image pickup unit 21 to generate compressed data. The compressed data is saved in a storage unit not shown. The compression processing control unit 24 is composed of a processor including hardware, such as a CPU or a DSP. The storage unit not shown is composed of at least part of a rewritable memory element, such as RAM, provided in the endoscope 2.

The selection unit 27 performs selection processing for selecting between a normal operation mode and a low power consumption operation mode in which low power consumption processing is executed, as an operation mode of the endoscope 2, and outputs a result of the selection processing to the endoscope control unit 23. The endoscope control unit 23 controls the image pickup unit 21 and the illumination unit 22 based on the result of the selection processing, and outputs information on specifics of the low power consumption processing to the first wireless communication unit 25A. When the low power consumption operation mode is selected, the image pickup unit 21 and the illumination unit 22 are controlled so that the power consumption of the endoscope 2 is reduced compared to when the normal operation mode is selected. The selection unit 27 is composed of a processor including hardware, such as a CPU or a DSP.

The first wireless communication unit 25A includes a wireless transmission circuit, not shown, configured to generate a signal to be wirelessly transmitted and a wireless reception circuit, not shown, configured to demodulate a wirelessly received signal, and transmits and receives a predetermined signal to/from the processor 3 by means of radio via the antenna 25B. The predetermined signal includes compressed data stored in the storage unit not shown, information on the specifics of the low power consumption processing, and a judgement result of a second judgement unit discussed later. Note that the first wireless communication unit 25A may be configured to be capable of wireless communication using multiple bands, e.g., 60 GHz band and 5 GHz band. In that case, the 60 GHz band is used for transmission and reception of compressed data, for example. The 5 GHz band is used for transmission and reception of information including selected parameters, for example.

The first wireless communication unit 25A further includes an environment detection circuit, not shown, configured to detect a state of a wireless communication environment. An amount of transferable data in wireless communication is defined by specifications of wireless communication and also varies depending on the wireless communication environment. The environment detection circuit outputs information on the detected state of the wireless communication environment to the endoscope control unit 23.

The input operation portion 28 is composed of a mechanical switch, a lever, and so on, not shown, provided at the operation portion 2B (see FIG. 1), generates an operation signal based on a user operation, and outputs the operation signal to the endoscope control unit 23. The user operation can be setting of the operation mode of the endoscope 2, for example.

The sensor unit 29 includes one or more sensors configured to measure environments outside and inside of the endoscope 2. In the present embodiment in particular, the sensor unit 29 includes temperature sensors for measuring temperatures at different parts of the endoscope 2. The different parts of the endoscope 2 are more specifically the image pickup unit 21, the illumination unit 22, the first wireless communication unit 25A, and the power source unit 26, the CPUs or DSPs constituting the respective ones of the endoscope control unit 23, the compression processing control unit 24 and the selection unit 27, and sensors other than the temperature sensors included in the sensor unit 29. Temperature sensors are positioned in at least one of these different parts and generate a temperature sensor signal corresponding to a measured temperature. The sensor unit 29 outputs a sensor signal including the temperature sensor signal to the endoscope control unit 23.

Configuration of the Processor

Next, the configuration of the processor 3 is described. As shown in FIG. 2, the processor 3 includes a processor control unit 31, a wireless receiver 32, an image processing unit 33, a video output unit 34, and a user interface unit (hereinafter denoted as a user IF unit) 35.

The wireless receiver 32 may be contained in the processor 3 or be configured separately from a body of the processor 3. In the latter case, the wireless receiver 32 is configured to be connected to the body of the processor 3 by a connector, not shown. FIG. 1 shows an example where the wireless receiver 32 is configured separately from the body of the processor 3.

The wireless receiver 32 includes a second wireless communication unit 32A and an antenna 32B. Note that since the wireless receiver 32 is a portion of the processor 3, the second wireless communication unit 32A can be said to be provided in the processor 3.

The second wireless communication unit 32A includes a wireless transmission circuit, not shown, configured to generate a signal to be wirelessly transmitted, and a wireless reception circuit, not shown, configured to demodulate a wirelessly received signal, and transmits and receives a predetermined signal to/from the endoscope 2 by means of radio via the antenna 32B. The predetermined signal includes compressed data transmitted by the first wireless communication unit 25A and information on specifics of low power consumption processing transmitted by the first wireless communication unit 25A, and a judgement result of the second judgement unit discussed later. Note that as with the first wireless communication unit 25A, the second wireless communication unit 32A may be configured to be capable of wireless communication using multiple bands, e.g., 60 GHz band and 5 GHz band.

The second wireless communication unit 32A further includes an environment detection circuit, not shown, configured to detect a state of a wireless communication environment. Functions of the environment detection circuit of the second wireless communication unit 32A are the same functions as functions of the environment detection circuit of the first wireless communication unit 25A.

The image processing unit 33 performs predetermined image processing on the compressed data received by the second wireless communication unit 32A. The image processing performed by the image processing unit 33 includes processing for decompressing compressed data to generate image data and development processing discussed later. Hereinafter, non-compressed image data generated by the image processing unit 33 will be referred to as decompressed image data. The image processing unit 33 outputs the decompressed image data to the video output unit 34. In the present embodiment, the image processing unit 33 outputs the decompressed image data also to the processor control unit 31.

When the selection unit 27 selects the low power consumption operation mode (hereinafter referred to as a period with the low power consumption operation mode selected), the image processing unit 33 performs image restoration processing for improving an image quality of a display image as the aforementioned image processing. Specifics of the image restoration processing will be discussed later.

The video output unit 34 converts the decompressed image data into a format that can be displayed on the monitor 4 and outputs the converted image data to the monitor 4 (see FIG. 1). The monitor 4 displays a display image corresponding to the decompressed image data.

The user IF unit 35 is an interface for accepting user operations. More specifically, the user IF unit 35 is composed of a front panel and various control-related buttons, for example, and outputs an operation signal based on a user operation to the processor control unit 31. The user operation can be designation of an observation mode of the endoscope 2, setting related to image display, and setting of the operation mode of the endoscope 2, for example. Note that the observation mode of the endoscope 2 may be configured to be selectable also at the input operation portion 28 of the endoscope 2.

The processor control unit 31 controls each circuit unit in the processor 3 and controls a power source unit, not shown, provided in the processor 3 to make the power source unit supply power to different parts in the processor 3. The processor control unit 31 is also able to give various instructions to the endoscope control unit 23 provided in the endoscope 2 through wireless communication between the endoscope 2 and the processor 3 based on an operation signal inputted from the user IF unit 35. The processor control unit 31 and the image processing unit 33 are each composed of a processor including hardware, such as a CPU or a DSP.

Configuration and Operation of the Endoscope Control Unit

Figure 3:
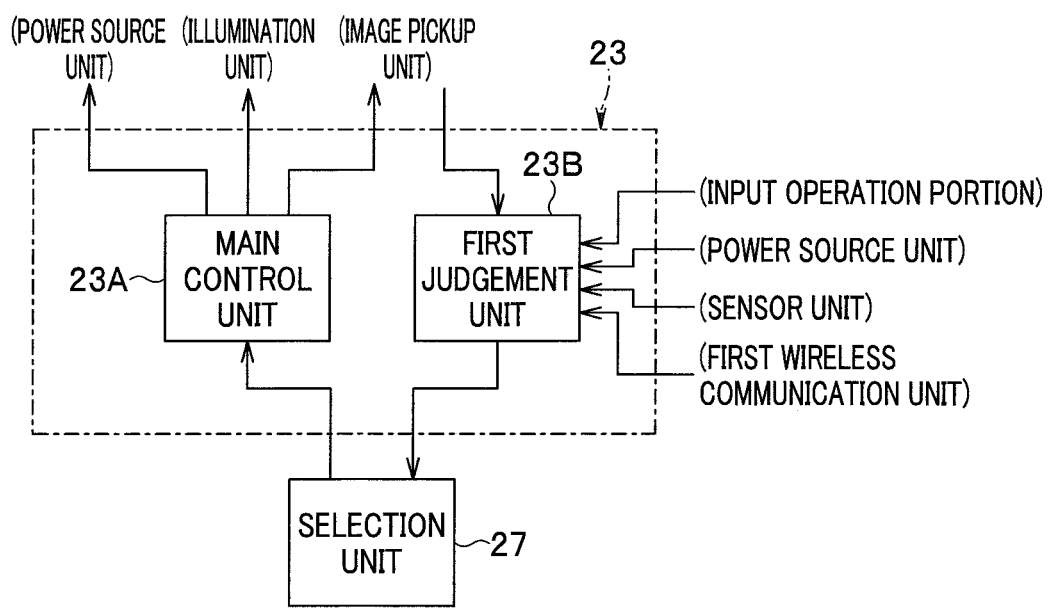
FIG. 3 is a functional block diagram showing configurations of an endoscope control unit and a selection unit in the first embodiment of the present invention.

Now referring to FIGS. 2 and 3, the configuration and operation of the endoscope control unit 23 are described in more detail. FIG. 3 is a functional block diagram showing configurations of the endoscope control unit 23 and the selection unit 27. As shown in FIG. 3, the endoscope control unit 23 includes a main control unit 23A and a first judgement unit 23B.

The first judgement unit 23B receives image data which is outputted by the image pickup unit 21, a battery level signal which is outputted by the power source unit 26, an operation signal which is outputted by the input operation portion 28, a sensor signal which is outputted by the sensor unit 29, and information on the state of wireless communication environment which is outputted by the environment detection circuit of the first wireless communication unit 25A. The first judgement unit 23B judges whether an execution condition of the low power consumption operation mode is met or not based on the above-described image data, signals and information, and outputs an obtained judgement result to the selection unit 27.

The selection unit 27 receives the judgement result from the first judgement unit 23B and a judgement result from the second judgement unit discussed later. The selection processing by the selection unit 27, that is, selection between the normal operation mode and the low power consumption operation mode, is made based on at least one of the judgement result from the first judgement unit 23B and the judgement result from the second judgement unit. The selection unit 27 outputs a result of selection processing to the main control unit 23A.

The main control unit 23A receives the result of selection processing. The main control unit 23A controls the image pickup unit 21, the illumination unit 22 and the power source unit 26 so that the image pickup unit 21, the illumination unit 22 and the power source unit 26 operate in accordance with the result of selection processing, that is, the selected operation mode. The main control unit 23A also outputs control specifics for the image pickup unit 21 and the illumination unit 22 to the image processing unit 33 provided in the processor 3 via wireless communication between the endoscope 2 and the processor 3.

The operation mode of the endoscope 2 is now described. During a period with the low power consumption operation mode selected, low power consumption processing for reducing the power consumption of the endoscope 2 is executed.

The illumination unit 22 is capable of executing, as the low power consumption processing, illumination light reduction processing which reduces illumination light compared to when the selection unit 27 selects the normal operation mode (hereinafter referred to as a period with the normal operation mode selected).

The image pickup unit 21 is capable of executing, as the low power consumption processing, frame rate reduction processing which reduces a frame rate of image data compared to in a period with the normal operation mode selected, and pixel count reduction processing which reduces a pixel count of image data compared to in a period with the normal operation mode selected.

During a period with the low power consumption operation mode selected, at least one of the illumination light reduction processing, the frame rate reduction processing and the pixel count reduction processing is executed.

Note that the low power consumption operation mode may include multiple operation modes which are different in specifics of the low power consumption processing executed. For example, the multiple operation modes may include a first operation mode, a second operation mode and a third operation mode. The first operation mode is an operation mode with lowest power consumption. The second operation mode is an operation mode with highest power consumption. The third operation mode is one or more operation modes with power consumption higher than the first operation mode and lower than the second operation mode. In this case, the main control unit 23A of the endoscope control unit 23 changes the specifics of the illumination light reduction processing, the frame rate reduction processing and the pixel count reduction processing, or changes a number of processings to be executed in accordance with the selected operation mode.

Configuration and Operation of the First Judgement Unit

Next, the configuration and operation of the first judgement unit 23B are described. The first judgement unit 23B includes at least one first detection unit and a detection result judgement unit 239. The at least one first detection unit detects a quantity of state associated with the execution condition of the low power consumption operation mode, and outputs an obtained detection result to the detection result judgement unit 239. The detection result judgement unit 239 judges whether the execution condition of the low power consumption operation mode is met or not based on the detection result from the at least one first detection unit.

Figure 4:
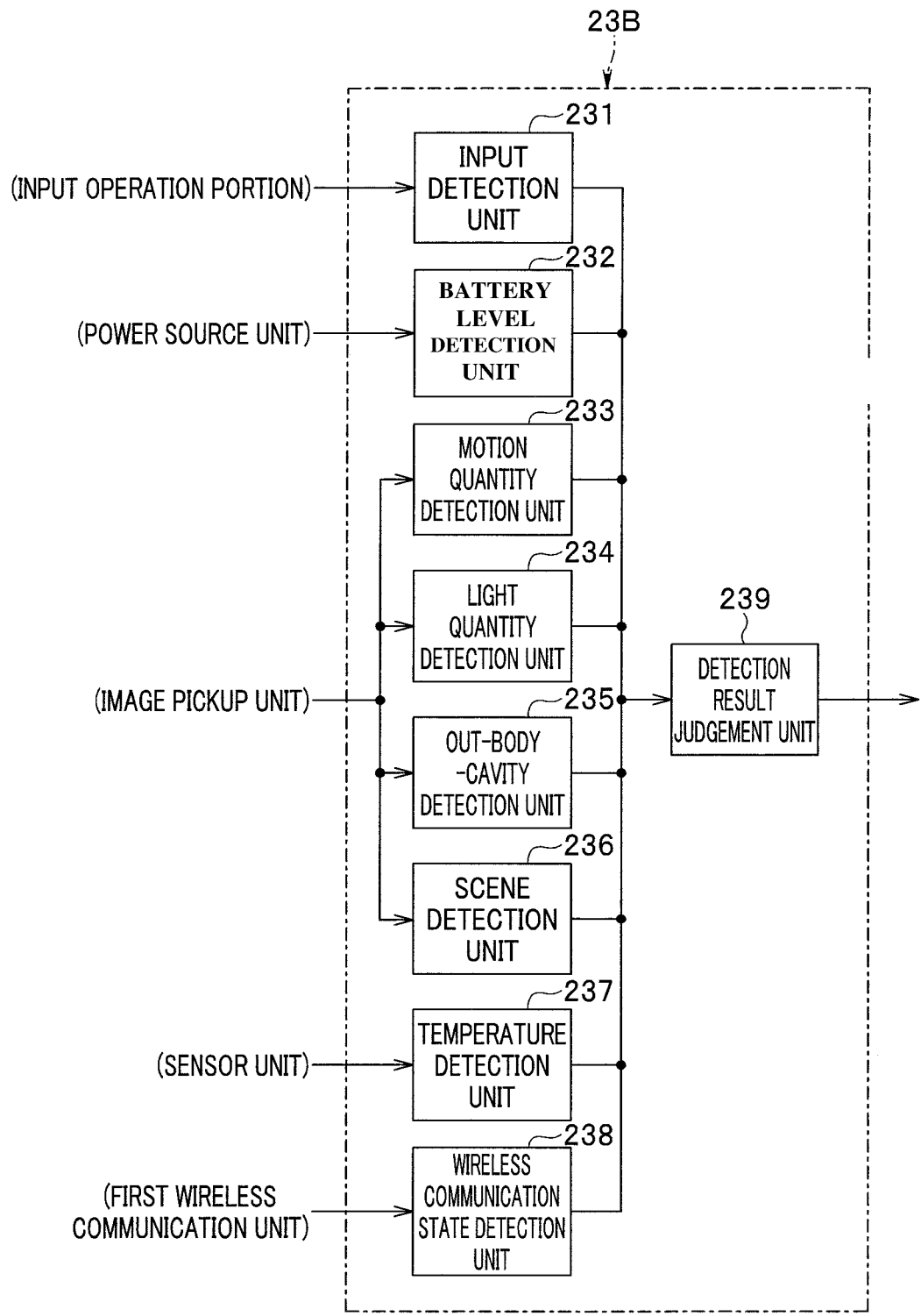
FIG. 4 is a functional block diagram showing an example of a configuration of a first judgement unit in the first embodiment of the present invention.

Referring to FIG. 4, an example of the configuration of the first judgement unit 23B is described below. In the example shown in FIG. 4, the first judgement unit 23B includes, as the at least one first detection unit, an input detection unit 231, a battery level detection unit 232, a motion quantity detection unit 233, a light quantity detection unit 234, an out-body-cavity detection unit 235, a scene detection unit 236, a temperature detection unit 237, and a wireless communication state detection unit 238. The detection result judgement unit 239 judges whether the execution condition of the low power consumption operation mode is met or not based on detection results from the input detection unit 231, the battery level detection unit 232, the motion quantity detection unit 233, the light quantity detection unit 234, the out-body-cavity detection unit 235, the scene detection unit 236, the temperature detection unit 237 and the wireless communication state detection unit 238.

The input detection unit 231 receives an operation signal which is outputted by the input operation portion 28. The input operation portion 28 is configured to select either one of the normal operation mode and the low power consumption operation mode, and to output an operation signal relevant to the selected operation mode. Note that if the low power consumption operation mode includes multiple operation modes, the input operation portion 28 is configured to select any one of the normal operation mode and the multiple operation modes and to output an operation signal relevant to the selected operation mode. The input detection unit 231 detects the operation signal relevant to the selected operation mode. If the operation signal relevant to the low power consumption operation mode is detected, the detection result judgement unit 239 judges that the execution condition of the low power consumption operation mode is met.

The battery level detection unit 232 receives a battery level signal which is outputted by the power source unit 26. The battery level detection unit 232 detects the battery level based on the battery level signal. When the battery level is equal to or lower than a predetermined threshold value, the detection result judgement unit 239 judges that the execution condition of the low power consumption operation mode is met.

The motion quantity detection unit 233, the light quantity detection unit 234, the out-body-cavity detection unit 235 and the scene detection unit 236 receive image data generated by the image pickup unit 21. The motion quantity detection unit 233 analyzes change in an image in multiple image data and detects a motion quantity of the object. The light quantity detection unit 234 analyzes change in brightness of the image in multiple image data and detects a change in light quantity of the image. When the insertion portion 2A is left without being used for observation, there is little change in the motion quantity of the object and the light quantity of the image. Accordingly, if the motion quantity of the object and the light quantity of the image are equal to or smaller than predetermined threshold values, respectively, the detection result judgement unit 239 judges that the execution condition of the low power consumption operation mode is met.

The out-body-cavity detection unit 235 analyzes a hue, e.g., reddishness, of the image which serves as a determination criterion on whether an image obtained by performing image pickup with the image pickup unit 21 represents outside of a body cavity or not, and detects whether the insertion portion 2A is inserted in a body or not. When the insertion portion 2A is positioned outside the body, a degree of the reddishness in the image, e.g., a number of reddish pixels, is low. Accordingly, when the degree of the reddishness of the image is equal to or smaller than a predetermined threshold, the detection result judgement unit 239 judges that the execution condition of the low power consumption operation mode is met.

The scene detection unit 236 analyzes the image data and detects an endoscope scene. Note that the endoscope scene can include a scene where the insertion portion 2A is moved at a relatively high speed in order to make the insertion portion 2A reach a target area, a scene where a search for any abnormal area is performed while moving the insertion portion 2A, a scene where a close observation or a certain measure is performed, for example. If the detected scene is not an important scene, the detection result judgement unit 239 judges that the execution condition of the low power consumption operation mode is met.

The temperature detection unit 237 receives a temperature sensor signal which is outputted by the temperature sensor in the sensor unit 29. The temperature detection unit 237 detects a temperature of the endoscope 2 based on the temperature sensor signal. The temperature of the endoscope 2 may be a temperature inside the endoscope 2 indicated by the temperature sensor signal. Alternatively, the temperature of the endoscope 2 may be a temperature on an outer surface of the endoscope 2, for example, a temperature on an outer surface of the grasping portion (see FIG. 1) of the operation portion 2B of the endoscope 2. The temperature on the outer surface can be estimated based on multiple temperature sensor signals which are outputted by temperature sensors positioned at different parts of the endoscope 2. If the temperature of the endoscope 2 is equal to or higher than a predetermined threshold value, the detection result judgement unit 239 judges that the execution condition of the low power consumption operation mode is met.

The wireless communication state detection unit 238 receives information on the state of the wireless communication environment detected by the environment detection circuit of the first wireless communication unit 25A. The wireless communication state detection unit 238 detects the state of the wireless communication environment based on the inputted information. Note that the state of the wireless communication environment may be detected as an amount of transferable data. In this case, the amount of transferable data may be computed by the environment detection circuit or may be computed by the wireless communication state detection unit 238. If the amount of transferable data is equal to or smaller than a predetermined threshold value, the detection result judgement unit 239 judges that the execution condition of the low power consumption operation mode is met.

In a case where the low power consumption operation mode includes multiple operation modes, the detection result judgement unit 239 can judge the execution condition for which one of the multiple operation modes is met by setting multiple threshold values when judging whether the execution condition of the low power consumption operation mode is met or not based on detection results from the battery level detection unit 232, the temperature detection unit 237 and the wireless communication state detection unit 238. Also, in a case where the low power consumption operation mode includes multiple operation modes, the detection result judgement unit 239 judges the execution condition for which one of the multiple operation modes is met according to a level of importance of the detected scene when judging the execution condition of the low power consumption operation mode is met or not based on a detection result from the scene detection unit 236.

When judging whether the execution condition of the low power consumption operation mode is met or not based on a detection result from a single first detection unit, the detection result judgement unit 239 outputs a judgement result which is based on the detection result to the selection unit 27. When judging whether the execution condition of the low power consumption operation mode is met or not based on detection results from two or more first detection units, the detection result judgement unit 239 judges whether the execution condition of the low power consumption operation mode is met or not using multiple detection results in a combined manner, and outputs an obtained judgement result to the selection unit 27.

Note that the configuration of the first judgement unit 23B is not limited to the example shown in FIG. 4. For example, the first judgement unit 23B may include only some of the multiple first detection units shown in FIG. 4 or may include first detection units other than the first detection units shown in FIG. 4. Also, the out-body-cavity detection unit 235 may be configured to receive a temperature sensor signal of the temperature sensor. In this case, the out-body-cavity detection unit 235 may determine whether an image represents outside of the body cavity or not based on the temperature sensor signal, thereby judging whether the execution condition of the low power consumption operation mode is met or not.

The sensor unit 29 may include a sensor for detecting the motion quantity of the endoscope 2 such as an acceleration sensor and a gyro sensor, or a humidity sensor, in addition to the temperature sensor. The sensor for detecting the motion quantity is configured to input a measurement result of the sensor to the motion quantity detection unit 233, for example. The humidity sensor is configured to input a measurement result of the sensor to the out-body-cavity detection unit 235, for example. The motion quantity detection unit 233 and the out-body-cavity detection unit 235 may judge whether the execution condition of the low power consumption operation mode is met or not based on the measurement results from the sensors, respectively.

Configuration and Operation of the Processor Control Unit

Figure 5:
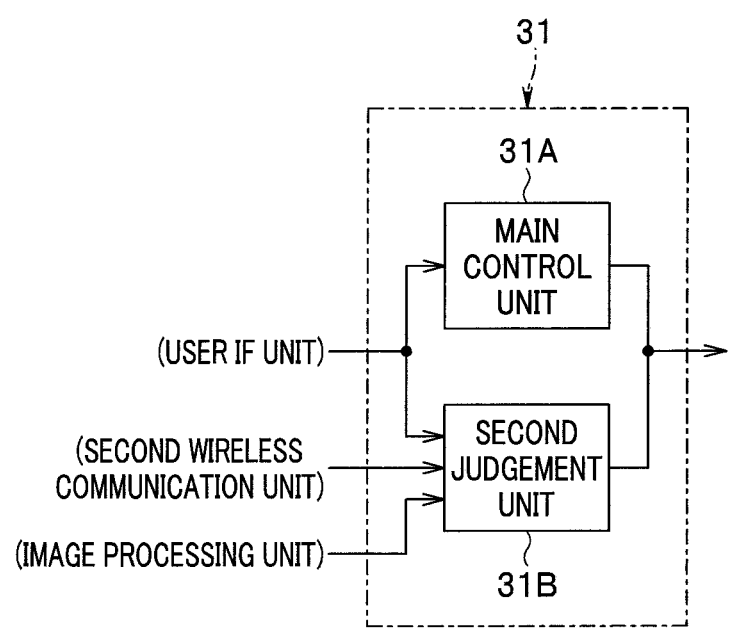
FIG. 5 is a functional block diagram showing a configuration of a processor control unit in the first embodiment of the present invention.

Now referring to FIGS. 2 and 5, the configuration and operation of the processor control unit 31 are described in detail. FIG. 5 is a functional block diagram showing a configuration of the processor control unit 31. As shown in FIG. 5, the processor control unit 31 includes a main control unit 31A and a second judgement unit 31B.

The main control unit 31A is a primary control unit of the processor control unit 31, configured to control each circuit unit in the processor 3. The main control unit 31A receives an operation signal which is outputted by the user IF unit 35.

The second judgement unit 31B receives image data which is outputted by the image processing unit 33, an operation signal which is outputted by the user IF unit 35, and information on the state of the wireless communication environment which is outputted by the environment detection circuit of the second wireless communication unit 32A. The second judgement unit 31B judges whether the execution condition of low power consumption operation mode is met or not based on the above-described image data, signals and information. The second judgement unit 31B also outputs an obtained judgement result to the selection unit 27 of the endoscope 2 via wireless communication between the endoscope 2 and the processor 3. That is, the second judgement unit 31B outputs the judgement result to the second wireless communication unit 32A. The second wireless communication unit 32A transmits the judgement result to the first wireless communication unit 25A via wireless communication between the first wireless communication unit 25A and the second wireless communication unit 32A. The first wireless communication unit 25A outputs the received judgement result to the selection unit 27.

Configuration and Operation of the Second Judgement Unit

Next, the configuration and operation of the second judgement unit 31B are described. The second judgement unit 31B includes at least one second detection unit and a detection result judgement unit 317. The at least one second detection unit detects a quantity of state associated with the execution condition of the low power consumption operation mode, and outputs an obtained detection result to the detection result judgement unit 317. The detection result judgement unit 317 judges whether the execution condition of the low power consumption operation mode is met or not based on the detection result from the at least one second detection unit.

Figure 6:
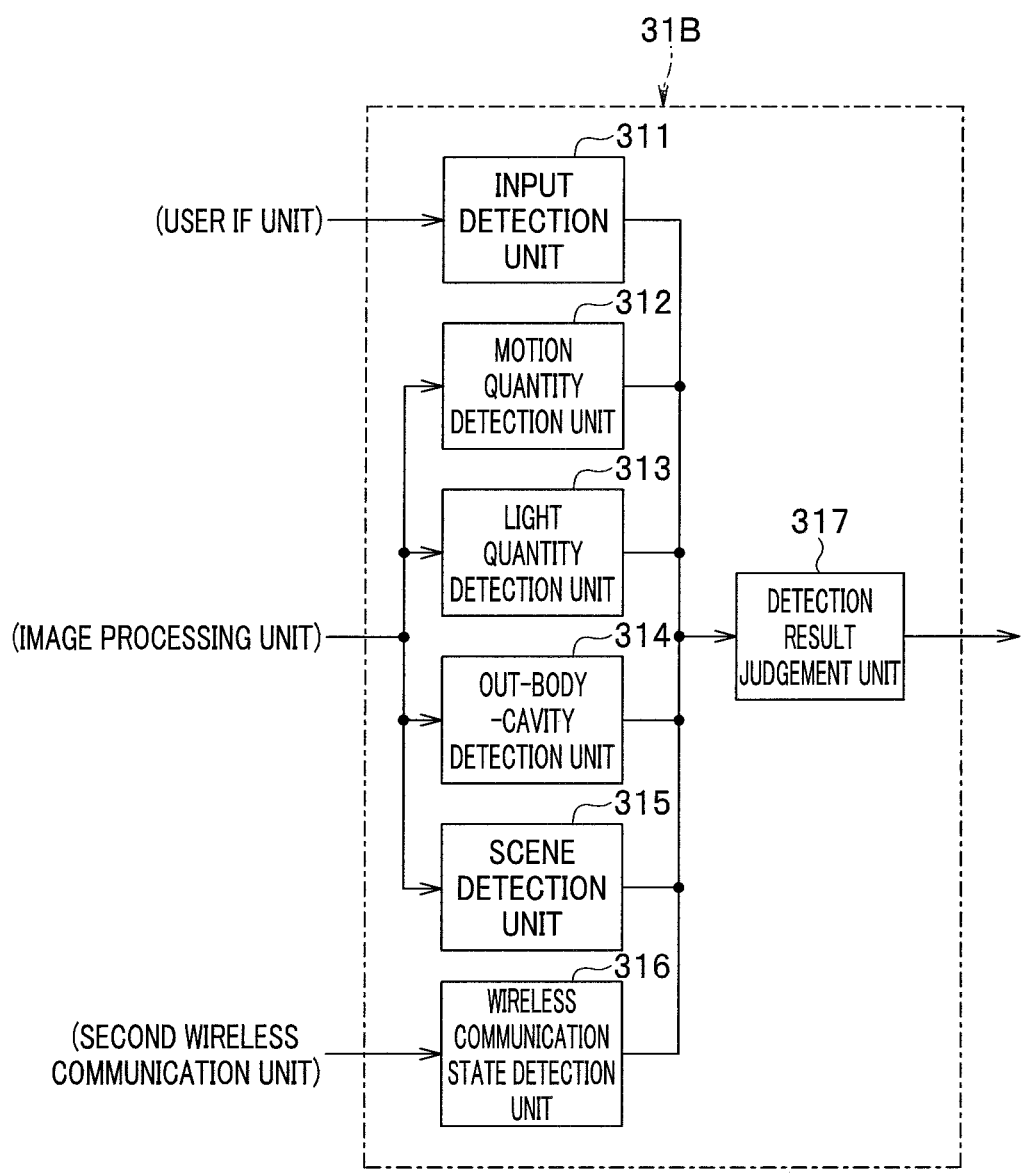
FIG. 6 is a functional block diagram showing a configuration of a second judgement unit in the first embodiment of the present invention.

Referring to FIG. 6, an example of the configuration of the second judgement unit 31B is described below. In the example shown in FIG. 6, the second judgement unit 31B includes, as the at least one second detection unit, an input detection unit 311, a motion quantity detection unit 312, a light quantity detection unit 313, out-body-cavity detection unit 314, a scene detection unit 315, and a wireless communication state detection unit 316. The detection result judgement unit 317 judges whether the execution condition of the low power consumption operation mode is met or not based on detection results from the input detection unit 311, the motion quantity detection unit 312, the light quantity detection unit 313, the out-body-cavity detection unit 314, the scene detection unit 315, and the wireless communication state detection unit 316.

The input detection unit 311 receives an operation signal which is outputted by the user IF unit 35. The user IF unit 35 is configured to select either one of the normal operation mode and the low power consumption operation mode and to output an operation signal relevant to the selected operation mode, as with the input operation portion 28. Note that if the low power consumption operation mode includes multiple operation modes, the user IF unit 35 is configured to select any one of the normal operation mode and the multiple operation modes and to output an operation signal relevant to the selected operation mode.

The motion quantity detection unit 312, the light quantity detection unit 313, the out-body-cavity detection unit 314, and the scene detection unit 315 receive image data decompressed by the image processing unit 33. Operations of the motion quantity detection unit 312, the light quantity detection unit 313, the out-body-cavity detection unit 314 and the scene detection unit 315 are the same as the operations of the motion quantity detection unit 233, light quantity detection unit 234, out-body-cavity detection unit 235 and the scene detection unit 236 of the first judgement unit 23B, respectively.

The wireless communication state detection unit 316 receives information on the state of the wireless communication environment detected by the environment detection circuit of the second wireless communication unit 32A. The operation of the wireless communication state detection unit 316 is the same as the operation of the wireless communication state detection unit 238 of the first judgement unit 23B.

The operation of the detection result judgement unit 317 based on the respective detection results from the input detection unit 311, the motion quantity detection unit 312, the light quantity detection unit 313, the out-body-cavity detection unit 314, the scene detection unit 315 and the wireless communication state detection unit 316 is the same as the operation of the detection result judgement unit 239 based on the respective detection results from the input detection unit 231, the motion quantity detection unit 233, the light quantity detection unit 234, the out-body-cavity detection unit 235, the scene detection unit 236 and the wireless communication state detection unit 238 of the first judgement unit 23B.

Note that the configuration of the second judgement unit 31B is not limited to the example shown in FIG. 6. For example, the second judgement unit 31B may include only some of the multiple second detection units shown in FIG. 6 or may include second detection units other than the second detection units shown in FIG. 4.

Low Power Consumption Processing

Now referring to FIGS. 2 and 3, the low power consumption processing is described. As mentioned previously, during a period with the low power consumption operation mode selected, at least one of illumination light reduction processing, frame rate reduction processing, and pixel count reduction processing is executed as the low power consumption processing. In a case where the low power consumption operation mode includes the first through the third operation modes described above, the main control unit 23A may change the light quantity of illumination light in a step-wise manner according to the selected operation mode so that the light quantity of illumination light in the illumination light reduction processing is minimized when the first operation mode is selected and is maximized when the second operation mode is selected.

Similarly, in a case where the low power consumption operation mode includes the first through the third operation modes described above, the main control unit 23A may change the frame count in a step-wise manner according to the selected operation mode so that the frame count in the frame rate reduction processing is minimized when the first operation mode is selected and is maximized when the second operation mode is selected.

Similarly, in a case where the low power consumption operation mode includes the first through the third operation modes described above, the main control unit 23A may change the pixel count in a step-wise manner according to the selected operation mode so that the pixel count in the pixel count reduction processing is minimized when the first operation mode is selected and is maximized when the second operation mode is selected.

Alternatively, the main control unit 23A may execute all of the three processings when the first operation mode is selected, execute one of the three processings when the second operation mode is selected, and execute at least one of the three processings when the third operation mode is selected. The main control unit 23A may also change the light quantity of illumination light, the frame count and the pixel count while changing the number of processings that are executed as mentioned above.

In the illumination light reduction processing, the main control unit 23A controls the illumination unit 22 in accordance with predetermined control specifics, and outputs information on an amount of reduction in illumination light to the image processing unit 33 of the processor 3 via wireless communication between the endoscope 2 and the processor 3. Information on the amount of reduction in illumination light is represented by a ratio of the light quantity of illumination light during execution of the illumination light reduction processing to the light quantity of illumination light during a period with the normal operation mode selected, for example.

In the frame rate reduction processing, the main control unit 23A controls the image pickup unit 21 in accordance with predetermined control specifics, and outputs information on the frame count in the frame rate reduction processing to the image processing unit 33 of the processor 3 via wireless communication between the endoscope 2 and the processor 3.

In the pixel count reduction processing, the main control unit 23A controls the image pickup unit 21 in accordance with predetermined control specifics, and outputs information on the pixel count in the pixel count reduction processing to the image processing unit 33 of the processor 3 via wireless communication between the endoscope 2 and the processor 3.

Information on the specifics of the low power consumption processing, that is, information on the amount of reduction in illumination light, information on the frame count and information on the pixel count may be outputted from the main control unit 23A to the image processing unit 33 by, for example, being stored in a header portion of wireless data transmitted and received between the first wireless communication unit 25A and the second wireless communication unit 32A. Note that information on the amount of reduction in illumination light may be outputted by the illumination unit 22. Similarly, information on the frame count and information on the pixel count may be outputted by the image pickup unit 21.

Configuration and Operation of the Image Processing Unit

Figure 7:
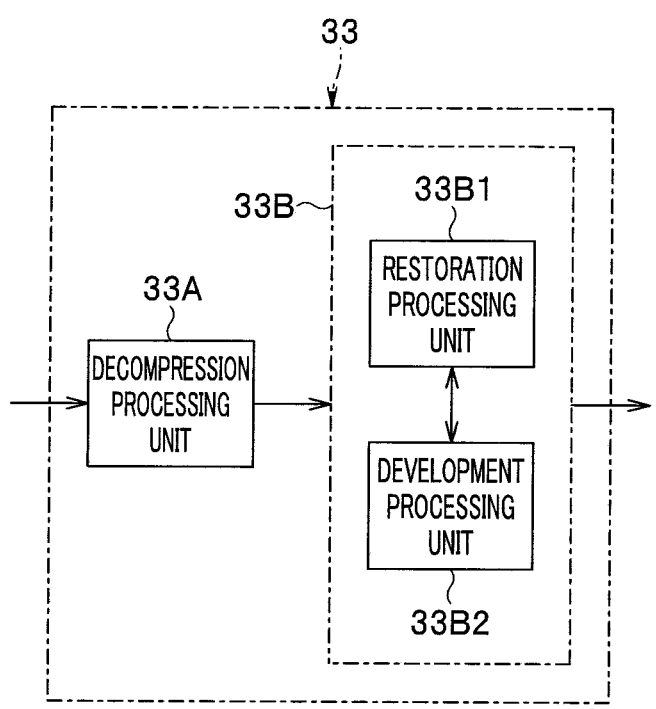
FIG. 7 is a functional block diagram showing a configuration of an image processing unit in the first embodiment of the present invention.

Now referring to FIG. 7, the configuration and operation of the image processing unit 33 are described in detail. FIG. 7 is a functional block diagram showing a configuration of the image processing unit 33. As shown in FIG. 7, the image processing unit 33 includes a decompression processing unit 33A and a main control unit 33B. The main control unit 33B includes a restoration processing unit 33B1 and a development processing unit 33B2.

The decompression processing unit 33A receives compressed data received by the second wireless communication unit 32A. The decompression processing unit 33A decompresses the compressed data to generate decompressed image data, and outputs the decompressed image data to the main control unit 33B.

The main control unit 33B receives the decompressed image data. When the selection unit 27 selects the normal operation mode, the decompressed image data is inputted to the development processing unit 33B2. The development processing unit 33B2 performs predetermined development processing on the decompressed image data and outputs the image data after being subjected to the development processing to the video output unit 34. The development processing may include processing for adjusting the brightness of the image, noise reduction processing for removing noise components of the image, and processing for adjusting a resolution of the image, for example.

When the selection unit 27 selects the low power consumption operation mode and illumination light reduction processing is in execution, information on the amount of reduction in illumination light is inputted to the restoration processing unit 33B1 and decompressed image data is inputted to the development processing unit 33B2. The restoration processing unit 33B1 controls the development processing unit 33B2 so as to perform image restoration processing relevant to the illumination light reduction processing based on the information on the amount of reduction in illumination light. In the present embodiment, image restoration processing which is performed when illumination light reduction processing is executed is at least one of gain boosting processing, noise reduction enhancement processing, and resolution enhancement processing.

The gain boosting processing is processing that improves image quality of a display image by increasing a correction factor for the brightness of the image in processing for adjusting the brightness of the image which is executed by the development processing unit 33B2 as development processing. The noise reduction enhancement processing is processing that improves the image quality of a display image by increasing an amount of noise reduction in the noise reduction processing which is executed by the development processing unit 33B2 as development processing. The resolution enhancement processing is processing that improves the image quality of a display image by increasing the resolution of the image in processing for adjusting the resolution of the image which is executed by the development processing unit 33B2 as development processing. The gain boosting processing, the noise reduction enhancement processing and the resolution enhancement processing are executed by changing of parameters in development processing by the restoration processing unit 33B1, for example.

In a case where the low power consumption operation mode includes the first through the third operation modes described above and the light quantity of illumination light is changed in a step-wise manner according to the selected operation mode, parameters of image restoration processing may be changed in a step-wise manner according to the selected operation mode or a number of image restoration processings for execution may be changed.

When the selection unit 27 selects the low power consumption operation mode and frame rate reduction processing is in execution, information on the frame count is inputted to the restoration processing unit 33B1 and decompressed image data is inputted to the development processing unit 33B2. The restoration processing unit 33B1 controls the development processing unit 33B2 so as to perform image restoration processing relevant to the frame rate reduction processing based on the information on the frame count. In the present embodiment, image restoration processing which is performed when frame rate reduction processing is executed is pseudo high frame rate creation processing. The pseudo high frame rate creation is processing that improves the image quality of a display image, more specifically, smoothness of motion of the image, by complementing frames. Complementing of frames is done by generating a new frame between two successive frames on the basis of the two frames, for example. The restoration processing unit 33B1 controls the development processing unit 33B2 so that pseudo high frame rate creation processing is performed on image data prior to being subjected to development processing or image data after being subjected to development processing.

In a case where the low power consumption operation mode includes the first through the third operation modes described above and the frame count is changed in a step-wise manner according to the selected operation mode, the number of frames complemented by pseudo high frame rate creation processing may be changed in a step-wise manner according to the selected operation mode. The image processing unit 33 may also be configured such that image data prior to being subjected to development processing is inputted to the restoration processing unit 33B1 and pseudo high frame rate creation processing is executed in the restoration processing unit 33B1. In this case, image data after being subjected to pseudo high frame rate creation processing is inputted to the development processing unit 33B2, and the development processing unit 33B2 performs predetermined development processing on the image data. Alternatively, the image processing unit 33 may be configured such that image data after being subjected to development processing is inputted to the restoration processing unit 33B1 and pseudo high frame rate creation processing is executed in the restoration processing unit 33B1.

When the selection unit 27 selects the low power consumption operation mode and pixel count reduction processing is in execution, information on the pixel count is inputted to the restoration processing unit 33B1 and decompressed image data is inputted to the development processing unit 33B2. The restoration processing unit 33B1 controls the development processing unit 33B2 so as to perform image restoration processing relevant to the pixel count reduction processing based on the information on the pixel count. In the present embodiment, image restoration processing which is performed when pixel count reduction processing is executed is at least one of image extension processing and edge enhancement processing. The image extension processing is processing that improves the image quality of a display image by adding a new pixel between pixels. The edge enhancement processing is processing that improves the image quality of a display image by emphasizing a contour portion in the image. The restoration processing unit 33B1 controls the development processing unit 33B2 so that at least one of image extension processing and edge enhancement processing is performed on image data after being subjected to development processing.

In a case where the low power consumption operation mode includes the first through the third operation modes described above and reduction processing in which the pixel count is changed in a step-wise manner according to the selected operation mode is executed, parameters of image restoration processing may be changed in a step-wise manner according to the selected operation mode or the number of image restoration processings for execution may be changed. The image processing unit 33 may also be configured such that image data prior to being subjected to development processing is inputted to the restoration processing unit 33B1 and image extension processing or edge enhancement processing is executed in the restoration processing unit 33B1. In this case, image data after being subjected to at least either one of image extension processing and edge enhancement processing is inputted to the development processing unit 33B2, and the development processing unit 33B2 performs predetermined development processing on the image data.

Actions and Effects

Next, actions and effects of the endoscope apparatus 1 according to the present embodiment are described. In the present embodiment, during a period with the low power consumption operation mode selected, at least one of illumination light reduction processing, frame rate reduction processing, and pixel count reduction processing is executed as low power consumption processing. The present embodiment can thereby reduce the power consumption of the endoscope 2.

However, when illumination light reduction processing, frame rate reduction processing and pixel count reduction processing are executed, the image quality of display image becomes lower compared to in a period with the normal operation mode selected if the image data obtained by performing image pickup with the image pickup unit 21 is displayed on the monitor 4 as a display image in a similar manner to during a period with the normal operation mode selected.

In the present embodiment, the image processing unit 33 performs image restoration processing that improves the image quality of the display image and that is relevant to illumination light reduction processing, frame rate reduction processing, or pixel count reduction processing during a period with the low power consumption operation mode selected. The present embodiment can thereby improve the image quality during execution of the low power consumption processing.

Note that in the present embodiment, the compression processing control unit 24 performs compression processing, which applies predetermined compression processing to the image data generated by the image pickup unit 21 to generate compressed data. When illumination light reduction processing, frame rate reduction processing and pixel count reduction processing are executed, image data becomes monotonous compared to in a period with the normal operation mode selected, resulting in a decrease in a data amount of the compressed data, that is, an amount of data that is transmitted and received by the first wireless communication unit 25A and the second wireless communication unit 32A. According to the present embodiment, the power consumption of the endoscope 2 can also be reduced in this way.

In the present embodiment, in order to decrease the data amount of compressed data to reduce the power consumption of the endoscope 2 as mentioned above, the compression processing control unit 24 may be capable of executing high-compression processing, which increases a compression rate compared to in a period with the normal operation mode selected, as low power consumption processing. In this case, during a period with the low power consumption operation mode selected, the endoscope control unit 23 may control the compression processing control unit 24 so that the compression processing control unit 24 executes high-compression processing. When high-compression processing is executed, the image processing unit 33 may improve the image quality of the display image by adjusting control parameters of decompression processing as image restoration processing.

Other effects of the present embodiment are described below. In the present embodiment, temperatures inside the endoscope 2 can be detected by temperature sensors positioned at different parts of the endoscope 2 or the temperature on an outer surface of the endoscope 2, such as a temperature on an outer surface of the grasping portion of the operation portion 2B of the endoscope 2, can be estimated. Moreover, in the present embodiment, low power consumption processing is executed during a period with the low power consumption operation mode selected, so that the temperatures at different parts of the endoscope 2 can be reduced compared to in a period with the normal operation mode selected. Accordingly, if the low power consumption operation mode is selected based on a detection result for the temperature of the endoscope 2, that is, if the low power consumption operation mode is selected due to increase in the temperatures at different parts of the endoscope 2, the power consumption of the endoscope 2 can be reduced and also the temperatures at different parts of the endoscope 2 can be reduced, thus preventing the different parts of the endoscope 2 from becoming hot to come to an abnormal stop or preventing the grasping portion of the operation portion 2B from becoming too hot for a user to grip the grasping portion.

Further, in the present embodiment, the state of the wireless communication environment can be detected by the environment detection circuit of the first wireless communication unit 25A or the environment detection circuit of the second wireless communication unit 32A. Also, in the present embodiment, low power consumption processing is executed during a period with the low power consumption operation mode selected, so that the data amount of compressed data is decreased compared to in a period with the normal operation mode selected. Accordingly, if the low power consumption operation mode is selected based on a detection result for the state of the wireless communication environment, that is, if the low power consumption operation mode is selected due to deterioration in the wireless communication environment, the power consumption of the endoscope 2 can be reduced and the data amount of compressed data, that is, the amount of data that is transmitted and received by the first wireless communication unit 25A and the second wireless communication unit 32A, is decreased to prevent an interruption of data transmission.

Second Embodiment

Next, an endoscope apparatus according to a second embodiment of the present invention is described. An endoscope apparatus 101 according to the present embodiment includes an endoscope 102, a processor 103 as a video processor, a universal cable 105 connecting the endoscope 102 and the processor 103, and a monitor, not shown, as a display unit connected with the processor 103. The monitor displays results of image processing, more specifically, images obtained by performing image pickup with the endoscope 102 and the like.

The endoscope 102 is basically similar in configuration to the endoscope 2 in the first embodiment. Although not shown, the endoscope 102 has an elongated insertion portion for insertion into a body cavity and an operation portion provided at a proximal end portion of the insertion portion. The universal cable 105 extends from the operation portion.

Configurations of the Endoscope and the Processor

Figure 8:
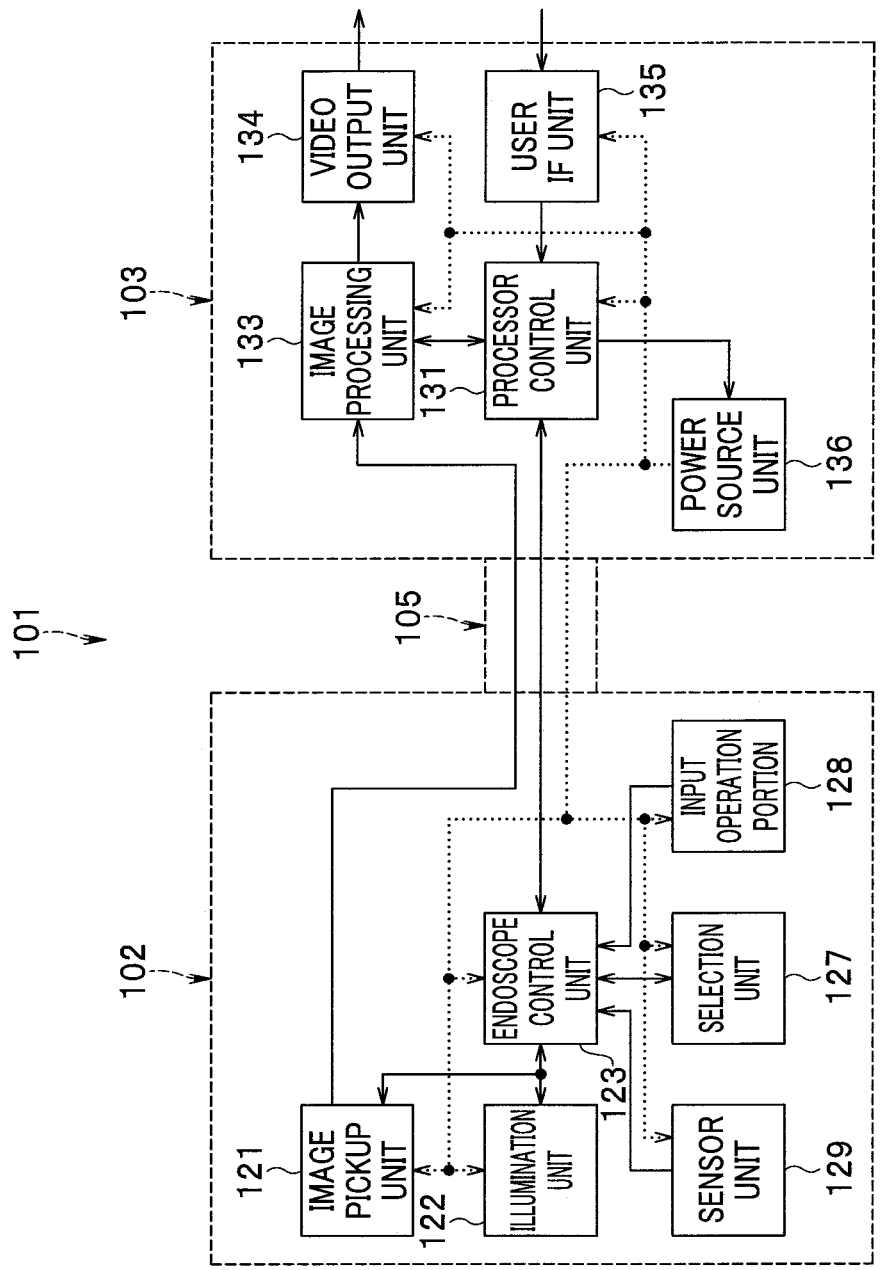
FIG. 8 is a functional block diagram showing a configuration of an endoscope apparatus according to a second embodiment of the present invention.

Referring to FIG. 8, configurations of the endoscope 102 and the processor 103 are described in detail below. FIG. 8 is a functional block diagram showing configurations of the endoscope 102 and the processor 103.

As shown in FIG. 8, the endoscope 102 includes an image pickup unit 121, an illumination unit 122, an endoscope control unit 123, a selection unit 127, an input operation portion 128, and a sensor unit 129. The processor 103 includes a processor control unit 131, an image processing unit 133, a video output unit 134, a user IF unit 135, and a power source unit 136. The endoscope control unit 123, the selection unit 127, the processor control unit 131 and the image processing unit 133 are each composed of a processor including hardware, such as a CPU or a DSP.

In the present embodiment, the power source unit 136 is configured to be able to supply electric power to the image pickup unit 121, the illumination unit 122, endoscope control unit 123, the selection unit 127, the input operation portion 128 and the sensor unit 129 of the endoscope 102, and to the processor control unit 131, the image processing unit 133, the video output unit 134 and the user IF unit 135 of the processor 103.

The endoscope control unit 123 controls each circuit unit in the endoscope 102 and controls the power source unit 136 to make the power source unit 136 supply electric power to different parts in the endoscope 102. Note that the endoscope control unit 123 may directly control the power source unit 136 or may control the power source unit 136 via the processor control unit 131.

The image pickup unit 121 performs image pickup of the object and generates image data. The illumination unit 122 illuminates the object. Configurations of the image pickup unit 121 and the illumination unit 122 are similar to the configurations of the image pickup unit 21 and the illumination unit 22 in the first embodiment, respectively. In the present embodiment, the image pickup unit 121 outputs the generated image data to the endoscope control unit 123 and the image processing unit 133 of the processor 103.

The selection unit 127 performs selection processing for selecting between the normal operation mode and the low power consumption operation mode in which low power consumption processing is executed, as the operation mode of the endoscope 102, and outputs a result of the selection processing to the endoscope control unit 123. The endoscope control unit 123 controls the image pickup unit 121 and the illumination unit 122 based on the result of the selection processing, and outputs information on specifics of the low power consumption processing to the image processing unit 133 of the processor 103. When the low power consumption operation mode is selected, the image pickup unit 121 and the illumination unit 122 are controlled so that the power consumption of the endoscope 102 is reduced compared to when the normal operation mode is selected.

Configurations of the input operation portion 128 and the sensor unit 129 are similar to the configurations of the input operation portion 28 and the sensor unit 29 in the first embodiment, respectively. In the present embodiment, the input operation portion 128 outputs a generated operation signal to the endoscope control unit 123, and the sensor unit 129 outputs a sensor signal including a temperature sensor signal to the endoscope control unit 123.

The image processing unit 133 performs predetermined image processing on the image data generated by the image pickup unit 121. The image processing performed by the image processing unit 133 includes development processing. Specifics of development processing are similar to those in the first embodiment. When the selection unit 127 selects the low power consumption operation mode (hereinafter referred to as a period with the low power consumption operation mode selected), the image processing unit 133 performs image restoration processing for improving the image quality of a display image displayed on a monitor, not shown. Specifics of the image restoration processing are similar to those in the first embodiment.

Configurations of the video output unit 134 and the user IF unit 135 are similar to the configurations of the video output unit 34 and the user IF unit 35 in the first embodiment, respectively. In the present embodiment, the user IF unit 135 outputs an operation signal based on a user operation to the processor control unit 131 and the endoscope control unit 123 of the endoscope 102.

The processor control unit 131 controls each circuit unit in the processor 103 and controls the power source unit 136 to make the power source unit 136 supply power to the different parts in the processor 103. The processor control unit 131 is also able to give various instructions to the endoscope control unit 123 provided in the endoscope 102 based on an operation signal inputted from the user IF unit 135.

Configuration and Operation of the Endoscope Control Unit

Figure 9:
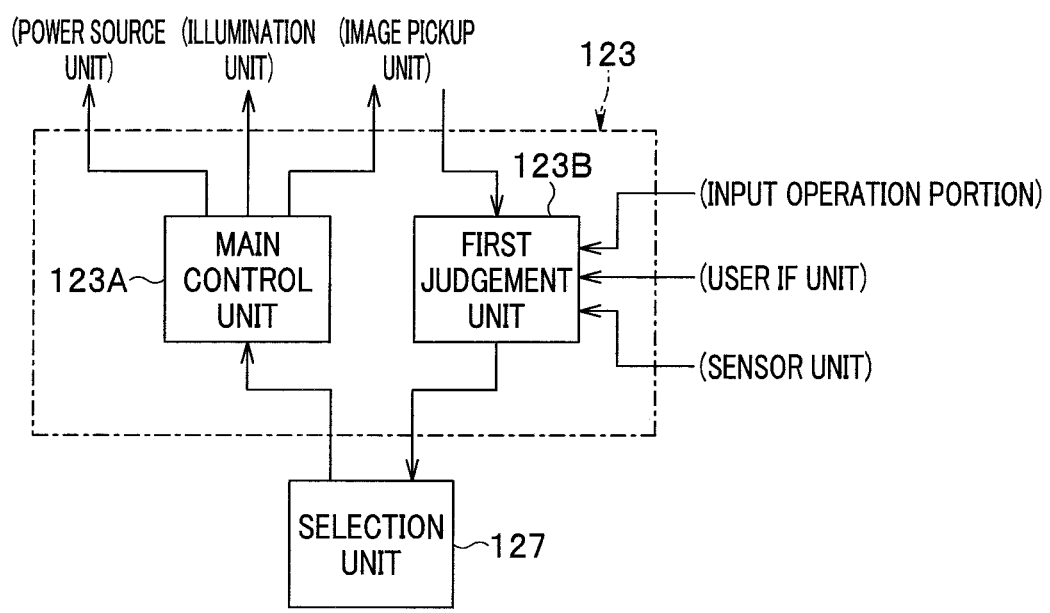
FIG. 9 is a functional block diagram showing configurations of an endoscope control unit and a selection unit in the second embodiment of the present invention.

Now referring to FIGS. 8 and 9, configuration and operation of the endoscope control unit 123 are described in more detail. FIG. 9 is a functional block diagram showing configurations of the endoscope control unit 123 and the selection unit 127. As shown in FIG. 9, the endoscope control unit 123 includes a main control unit 123A and a first judgement unit 123B.

The first judgement unit 123B receives image data which is outputted by the image pickup unit 121, operation signals which is outputted by the input operation portion 128 and the user IF unit 135, and a sensor signal which is outputted by the sensor unit 129. The first judgement unit 123B judges whether the execution condition of the low power consumption operation mode is met or not based on the above-described image data and signals, and outputs an obtained judgement result to the selection unit 127.

The selection unit 127 receives the judgement result from the first judgement unit 123B. Selection processing by the selection unit 127, that is, selection between the normal operation mode and the low power consumption operation mode, is made based on the judgement result from the first judgement unit 123B. The selection unit 127 outputs a result of selection processing to the main control unit 123A.

The main control unit 123A receives the result of selection processing. The main control unit 123A controls the image pickup unit 121, the illumination unit 122 and the power source unit 136 so that the image pickup unit 121, the illumination unit 122 and the power source unit 136 operate in accordance with the result of selection processing, that is, the selected operation mode. The main control unit 123A also outputs control specifics for the image pickup unit 121 and the illumination unit 122 to the image processing unit 133 provided in the processor 103.

During a period with the low power consumption operation mode selected, low power consumption processing for reducing the power consumption of the endoscope 102 is executed. The illumination unit 122 is capable of executing the illumination light reduction processing described in the first embodiment as low power consumption processing, as with the illumination unit 22 in the first embodiment. The image pickup unit 121 is capable of executing frame rate reduction processing and pixel count reduction processing as low power consumption processing, as with the image pickup unit 121 in the first embodiment. Specifics of the illumination light reduction processing, the frame rate reduction processing and the pixel count reduction processing are similar to those in the first embodiment.

Configuration and Operation of the First Judgement Unit

Next, configuration and operation of the first judgement unit 123B are described. The first judgement unit 123B includes at least one first detection unit and a detection result judgement unit 1237 as with the first judgement unit 23B in the first embodiment. Operations of the at least one first detection unit and the detection result judgement unit 1237 are similar to the operations of the at least one first detection unit and the detection result judgement unit 239 in the first embodiment.

Figure 10:
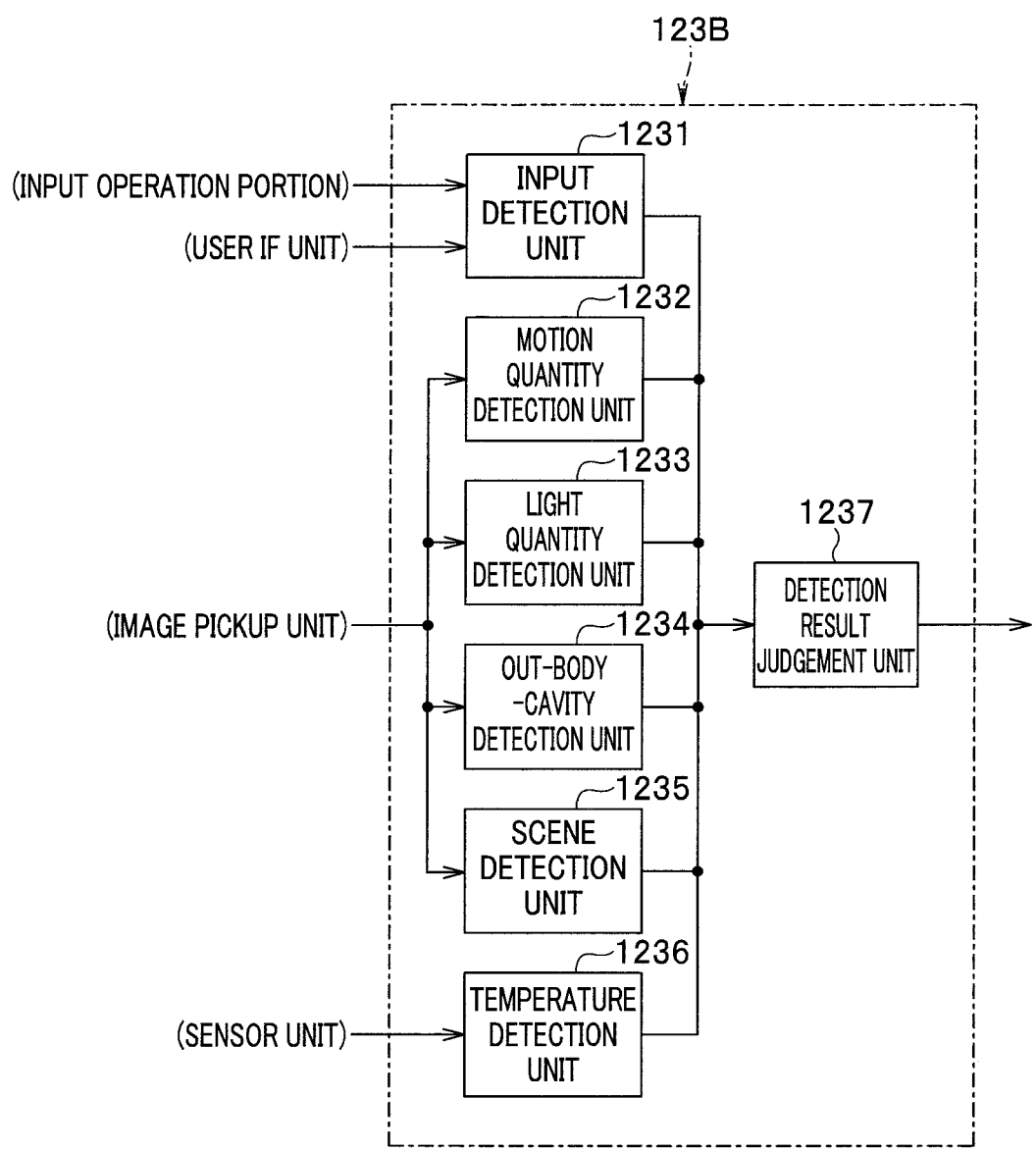
FIG. 10 is a functional block diagram showing an example of the configuration of a first judgement unit in the second embodiment of the present invention.

Referring to FIG. 10, an example of the configuration of the first judgement unit 123B is described below. In the example shown in FIG. 10, the first judgement unit 123B includes, as the at least one first detection unit, an input detection unit 1231, a motion quantity detection unit 1232, a light quantity detection unit 1233, an out-body-cavity detection unit 1234, a scene detection unit 1235, and a temperature detection unit 1236. The detection result judgement unit 1237 judges whether the execution condition of the low power consumption operation mode is met or not based on detection results from the input detection unit 1231, the motion quantity detection unit 1232, the light quantity detection unit 1233, the out-body-cavity detection unit 1234, the scene detection unit 1235, and the temperature detection unit 1236.

The input detection unit 1231 receives operation signals which is outputted by the input operation portion 128 and the user IF unit 135. Operation of the input detection unit 1231 is similar to the operations of the input detection units 231, 311 in the first embodiment.

The motion quantity detection unit 1232, the light quantity detection unit 1233, the out-body-cavity detection unit 1234 and the scene detection unit 1235 receive image data generated by the image pickup unit 121. Operations of the motion quantity detection unit 1232, the light quantity detection unit 1233, the out-body-cavity detection unit 1234 and the scene detection unit 1235 are similar to the operations of the motion quantity detection unit 233, the light quantity detection unit 234, the out-body-cavity detection unit 235 and the scene detection unit 236 in the first embodiment.

The temperature detection unit 1236 receives a temperature sensor signal which is outputted by a temperature sensor of the sensor unit 129. Operation of the temperature detection unit 1236 is similar to the operation of the temperature detection unit 237 in the first embodiment.

Configuration and Operation of the Image Processing Unit

Figure 11:
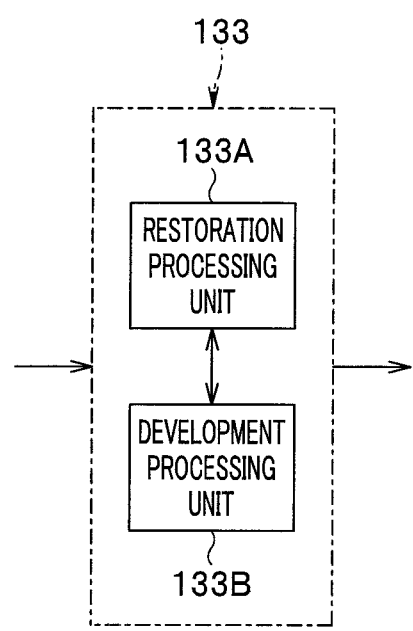
FIG. 11 is a functional block diagram showing a configuration of an image processing unit in the second embodiment of the present invention.

Now referring to FIG. 11, configuration and operation of the image processing unit 133 are described in detail. FIG. 11 is a functional block diagram showing a configuration of the image processing unit 133. As shown in FIG. 11, the image processing unit 133 includes a restoration processing unit 133A and a development processing unit 133B.

When the selection unit 127 selects the normal operation mode, image data generated by the image pickup unit 121 is inputted to the development processing unit 133B. The development processing unit 133B performs predetermined development processing on the image data and outputs the image data after being subjected to the development processing to the video output unit 134.

When the selection unit 127 selects the low power consumption operation mode and illumination light reduction processing is in execution, information on the amount of reduction in illumination light which is outputted by the main control unit 123A is inputted to the restoration processing unit 133A, and image data is inputted to the development processing unit 133B. The restoration processing unit 133A controls the development processing unit 133B so as to perform image restoration processing relevant to the illumination light reduction processing based on the information on the amount of reduction in illumination light. Specifics of the image restoration processing relevant to illumination light reduction processing are the same as those in the first embodiment.

When the selection unit 127 selects the low power consumption operation mode and frame rate reduction processing is in execution, information on the frame count which is outputted by the main control unit 123A is inputted to the restoration processing unit 133A and decompressed image data is inputted to the development processing unit 133B. The restoration processing unit 133A controls the development processing unit 133B so as to perform image restoration processing relevant to the frame rate reduction processing based on the information on the frame count. Specifics of the image restoration processing relevant to the frame rate reduction processing are the same as those in the first embodiment.

When the selection unit 127 selects the low power consumption operation mode and pixel count reduction processing is in execution, information on the pixel count which is outputted by the main control unit 123A is inputted to the restoration processing unit 133A and decompressed image data is inputted to the development processing unit 133B. The restoration processing unit 133A controls the development processing unit 133B so as to perform image restoration processing relevant to the pixel count reduction processing based on the information on the pixel count. Specifics of the image restoration processing relevant to the pixel count reduction processing are the same as those in the first embodiment.

The configuration of the endoscope apparatus 101 according to the present embodiment is not limited to the example described with reference to FIGS. 8 to 11. For example, in the present embodiment, the selection unit 127 may be provided in the processor 103 and the main control unit and a second judgement unit may be provided in the processor control unit 131. In this case, the endoscope control unit 123 may not include the main control unit 123A and the first judgement unit 123B. Configuration and operation of the second judgement unit are similar to the configuration and operation of the first judgement unit 123B. A judgement result of the second judgement unit is inputted to the selection unit 127. Selection processing by the selection unit 127, that is, selection between the normal operation mode and the low power consumption operation mode, is made based on the judgement result from the second judgement unit. The selection unit 127 outputs a result of the selection processing to the endoscope control unit 123.

Other configurations, actions and effects in the present embodiment are similar to those in the first embodiment.

The present invention is not limited to the above-described embodiments; various modifications, alterations and the like are possible without departing from the scope of the present invention.

What is claimed is:

1. An endoscope apparatus comprising:
   an image pickup device configured to perform image pickup of an object and generate image data;
   an illumination element configured to illuminate the object;
   a power source configured to supply electric power to the image pickup device and the illumination element;
   a monitor configured to display a display image corresponding to the image data; and
   a processor,
   wherein the processor is configured to:
   perform selection processing for selecting between a normal operation mode and a low power consumption operation mode in which low power consumption processing is executed, and
   perform image processing on the image data,
   the illumination element is capable of executing, as the low power consumption processing, illumination light reduction processing which reduces illumination light compared to when the processor selects the normal operation mode,
   the image pickup device is capable of executing, as the low power consumption processing, frame rate reduction processing which reduces a frame rate of the image data compared to when the processor selects the normal operation mode, and pixel count reduction processing which reduces a pixel count of the image data compared to when the processor selects the normal operation mode, and
   when the processor selects the low power consumption operation mode, at least one of the illumination light reduction processing, the frame rate reduction processing and the pixel count reduction processing is executed, and the processor detects which one or ones of the illumination light reduction processing, the frame rate reduction processing and the pixel count reduction processing is or are executed as the low power consumption processing and performs image restoration processing for improving an image quality of the display image in accordance with an obtained detection result.

2. The endoscope apparatus according to claim 1, wherein the image restoration processing which is performed when the illumination light reduction processing is executed is at least one of gain boosting processing for increasing a correction factor for a brightness of an image, noise reduction enhancement processing for increasing an amount of noise reduction in noise reduction processing which removes noise components of the image, and resolution enhancement processing for increasing a resolution of the image.

3. The endoscope apparatus according to claim 1, wherein the image restoration processing which is performed when the frame rate reduction processing is executed is pseudo high frame rate creation processing for interpolating frames.

4. The endoscope apparatus according to claim 1, wherein the image restoration processing which is performed when the pixel count reduction processing is executed is at least one of image extension processing for adding a new pixel between pixels and edge enhancement processing for emphasizing a contour portion in an image.

5. The endoscope apparatus according to claim 1, wherein the low power consumption operation mode includes a plurality of operation modes which are different from each other in specifics of the low power consumption processing executed.

6. The endoscope apparatus according to claim 1, wherein
the processor is further configured to compress the image data to generate compressed data, and
the processor decompresses the compressed data to generate the image data and performs the image restoration processing on the image data generated by decompressing the compressed data.

7. The endoscope apparatus according to claim 1, further comprising:
an endoscope;
a video processor; and
a universal cable connecting the endoscope and the video processor;
wherein the image pickup device and the illumination element are provided in the endoscope,
the power source is provided in the video processor,
the monitor is connected with the processor, and
the processor is provided at least in the video processor out of the endoscope and the video processor.

8. An endoscope apparatus comprising:
an endoscope;
a video processor physically separated from the endoscope; and
a monitor configured to display a display image corresponding to image data obtained by performing image pickup with the endoscope,
wherein the endoscope comprises:
an image pickup device configured to perform image pickup of an object and generate the image data;
an illumination element configured to illuminate the object;
a power source configured to supply electric power to the image pickup device and the illumination element;
a first processor; and
a first wireless communication circuit,
the first processor is configured to:
perform selection processing for selecting between a normal operation mode and a low power consumption operation mode in which low power consumption processing is executed,
compress the image data to generate compressed data, and
judge whether an execution condition of the low power consumption operation mode is met or not,
the first wireless communication circuit transmits the compressed data and information on specifics of the low power consumption processing,
the video processor comprises:
a second wireless communication circuit configured to receive the transmitted compressed data and information on specifics of the low power consumption processing; and
a second processor,
the second processor is configured to:
perform image processing on the image data generated by decompressing the compressed data; and
judge whether the execution condition of the low power consumption operation mode is met or not,
the first processor detects a quantity of state associated with the execution condition of the low power consumption operation mode, and judges whether the execution condition of the low power consumption operation mode is met or not based on an obtained detection result,
the second processor detects a quantity of state associated with the execution condition of the low power consumption operation mode, judges whether the execution condition of the low power consumption operation mode is met or not based on an obtained detection result, and outputs an obtained judgement result to the first processor via wireless communication between the first wireless communication circuit and the second wireless communication circuit, and
the first processor performs the selection processing based on at least one of the judgement result from the first processor and the judgement result from the second processor.

9. The endoscope apparatus according to claim 8, wherein
the illumination element is capable of executing, as the low power consumption processing, illumination light reduction processing which reduces illumination light compared to when the first processor selects the normal operation mode,
the image pickup device is capable of executing, as the low power consumption processing, frame rate reduction processing which reduces a frame rate of the image data compared to when the first processor selects the normal operation mode, and pixel count reduction processing which reduces a pixel count of the image data compared to when the first processor selects the normal operation mode, and
when the first processor selects the low power consumption operation mode, at least one of the illumination light reduction processing, the frame rate reduction processing and the pixel count reduction processing is executed, and the second processor performs image restoration processing that improves an image quality of the display image and that is relevant to the illumination light reduction processing, the frame rate reduction processing and the pixel count reduction processing.

10. An endoscope comprising:
an image pickup device configured to perform image pickup of an object and generate image data;
an illumination element configured to illuminate the object;
a power source configured to supply electric power to the image pickup device and the illumination element; and
a processor configured to perform selection processing for selecting between a normal operation mode and a low power consumption operation mode in which low power consumption processing is executed,
wherein the illumination element is capable of executing, as the low power consumption processing, illumination light reduction processing which reduces illumination light compared to when the processor selects the normal operation mode,
the image pickup device is capable of executing, as the low power consumption processing, frame rate reduction processing which reduces a frame rate of the image data compared to when the processor selects the normal operation mode, and pixel count reduction processing which reduces a pixel count of the image data compared to when the processor selects the normal operation mode, and when the processor selects the low power consumption operation mode, at least one of the illumination light reduction processing, the frame rate reduction processing and the pixel count reduction processing is executed, and the processor outputs information on specifics of the low power consumption processing to a video processor connected with a display unit configured to display a display image corresponding to the image data so that the video processor can detect which one or ones of the illumination light reduction processing, the frame rate reduction processing and the pixel count reduction processing is or are executed as the low power consumption processing and perform image restoration processing for improving an image quality of the display image in accordance with an obtained detection result.

11. A video processor connected with a monitor configured to display a display image corresponding to image data generated by an endoscope, the video processor comprising:

a processor configured to receive the image data transmitted by the endoscope and to perform image processing on the image data, wherein the endoscope is capable of executing, as low power consumption processing, illumination light reduction processing which reduces illumination light of an illumination element of the endoscope, frame rate reduction processing which reduces a frame rate of the image data, and pixel count reduction processing which reduces a pixel count of the image data, and outputs information on specifics of the low power consumption processing to the processor, and the processor detects which one or ones of the illumination light reduction processing, the frame rate reduction processing and the pixel count reduction processing is or are executed as the low power consumption processing, and performs image restoration processing for improving an image quality of the display image in accordance with an obtained detection result.

12. A restoration method for restoring image data acquired with an image pickup device of an endoscope, the restoration method comprising:

performing selection processing for selecting between a normal operation mode and a low power consumption operation mode in which low power consumption processing is executed, as an operation mode in which electric power is supplied to the image pickup device and an illumination element of the endoscope;

performing image processing on the image data; and displaying a display image corresponding to the image data, wherein the illumination element is capable of executing, as the low power consumption processing, illumination light reduction processing which reduces illumination light compared to when the normal operation mode is selected, and the image pickup device is capable of executing, as the low power consumption processing, frame rate reduction processing which reduces a frame rate of the image data compared to when the normal operation mode is selected, and pixel count reduction processing which reduces a pixel count of the image data compared to when the normal operation mode is selected, and the restoration method further comprises:

when the low power consumption operation mode is selected, executing at least one of the illumination light reduction processing, the frame rate reduction processing and the pixel count reduction processing, detecting which one or ones of the illumination light reduction processing, the frame rate reduction processing and the pixel count reduction processing is or are executed as the low power consumption processing, and performing image restoration processing for improving an image quality of the display image in accordance with an obtained detection result.

* * * * *